United States Patent [19]
Chwalisz et al.

[11] Patent Number: 5,811,416
[45] Date of Patent: Sep. 22, 1998

[54] ENDOTHELIN ANTAGONIST AND/OR ENDOTHELIN SYNTHASE INHIBITOR IN COMBINATION WITH A PROGESTIN, AN ESTROGEN, A CYCLOOXYGENASE INHIBITOR, OR A NITRIC ACID DONOR OR SUBSTRATE

[75] Inventors: Kristof Chwalisz, Berlin, Germany; Robert E. Garfield, Friendswood, Tex.

[73] Assignees: Board of Regents The University of Texas System, Austin, Tex.; Schering Aktiengesellschaft, Berlin, Germany

[21] Appl. No.: 437,462

[22] Filed: May 8, 1995

Related U.S. Application Data

[63] Continuation-in-part of Ser. No. 254,584, Jun. 6, 1994, abandoned.

[51] Int. Cl.⁶ .................. A61K 31/56; A61K 31/225; A61K 31/195
[52] U.S. Cl. .................. 514/177; 514/548; 514/565; 514/899
[58] Field of Search .................. 514/177, 548, 514/565, 899

[56] References Cited

U.S. PATENT DOCUMENTS

| | | | |
|---|---|---|---|
| 5,260,276 | 11/1993 | Cody et al. | 514/14 |
| 5,378,715 | 1/1995 | Stein et al. | 514/329 |
| 5,508,045 | 4/1996 | Harrison et al. | 424/608 |

FOREIGN PATENT DOCUMENTS

| | | |
|---|---|---|
| 93/10144 | 5/1993 | WIPO . |
| 93/25580 | 12/1993 | WIPO . |
| 95/00537 | 1/1995 | WIPO . |
| 95/02408 | 1/1995 | WIPO . |
| 95/13802 | 5/1995 | WIPO . |

OTHER PUBLICATIONS

Garfield et al., "Reversal of Preeclampsia Symptoms Induced in Rats by Nitric Oxide Inhibition With L–Arginine, Steroid Hormones and an Endothelin Antagonist," Soc. Gynecol. Invest. Abst. p. 384 (1994).

Chwalisz et al., "Estradiol Inhibits the Onapristone–Induced Preterm Parturition in Guinea Pigs by Blocking Cervical Ripening," J. Soc. Gynecol. Invest., vol. 2, No. 2, Mar. 1995.

Chwalisz et al., "Role of Progesterone During Pregnancy: Models of Parturition and Preeclampsia," Z. Geburtshilfe Perinatol, vol. 198, No. 5–5, pp. 170–180, 1994.

Richard et al., "In Vivo Evidence of an Endothelin–Induced Vasopressor Tone After Inhibition of Nitric Oxide Synthesis in Rats," Circulation, vol. 91, No. 3, pp. 771–775, Feb. 1995.

Yallampalli et al., Inhibition of Nitric Oxide Synthesis in Rats During Pregnancy Produces Signs Similar to Those of Preeclampsia, Am J Obstet. Gynecol, vol. 169, No. 5, pp. 1316–1320, 1993.

CA 121: 50830, Veniant et al., 1994.

CA 120: 271192, Cody et al, 1993.

CA 99: 169887, Szekenes–Bartho et al., 1983.

*Primary Examiner*—Kimberly Jordan
*Attorney, Agent, or Firm*—Millen, White, Zelano & Branigan, P.C.

[57] ABSTRACT

A pharmaceutical composition for and methods of treatment of menstrual disorders, e.g., dysmenorrhea, in a non-pregnant female, preterm labor, preeclampsia and/or fetal growth retardation in a pregnant female mammal, treatment of atherosclerotic vascular disease and hypertension in males as well as females, and for hormone replacement therapy in peri- and post-menopausal females, comprising administering effective amounts of an endothelin antagonist and/or an endothelin synthase inhibitor or both, in combination with a progestin, and/or an estrogen, and/or a cyclooxygenase inhibitor, and/or a nitric oxide donor and/or nitric oxide substrate, to prevent and/or ameliorate said conditions, are disclosed. In the method aspects, the endothelin antagonist and/or endothelin synthase inhibitor can be administered alone for treatment of menstrual disorders, e.g., dysmenorrhea, in a non-pregnant female, preterm labor, preeclampsia and/or fetal growth retardation in a pregnant female mammal. Further, methods for screening compounds for such treatments are disclosed.

64 Claims, 3 Drawing Sheets

ENDOTHELIN ANTAGONIST AND/OR
ENDOTHELIN SYNTHASE INHIBITOR IN
COMBINATION WITH A PROGESTIN, AN
ESTROGEN, A CYCLOOXYGENASE
INHIBITOR, OR A NITRIC ACID DONOR OR
SUBSTRATE

This application is a continuation-in-part of U.S. Ser. No. 08/254,584, filed Jun. 6, 1994, now abandoned.

BACKGROUND OF THE INVENTION

This invention relates to a method for the treatment of uterine contractility disorders, such as preterm labor, abortion, dysmenorrhea and menstrual disorders and to the treatment of preeclampsia with an endothelin antagonist, an endothelin synthase inhibitor, or both, alone or further in combination with a progesterone or a cyclooxygenase inhibitor. In addition, the invention relates to the treatment of atherosclerotic vascular disease and hypertension in males as well as females with an endothelin antagonist and/or an endothelin synthase inhibitor in combination with estrogens and/or progestins, and as a component of hormone replacement therapy in peri- and post-menopausal females.

Preterm labor, and subsequent preterm birth is a major problem of perinatology in general. By definition, a term gestation in human is one that is completed between 38 and 42 weeks. However, in approximately 5 to 15% of women, birth occurs prematurely, i.e., before 37 completed weeks. In humans, premature birth is responsible for 75% of infant mortality and 50% of long-term neurological handicaps (Creasy, 1989). To date, there are no effective methods of treatment and prevention for either preterm labor or preterm birth. The current use of β-mimetics in the treatment of preterm labor is only of limited value. The meta-analyses of the results of controlled trials show little or no effect of β-mimetics on the frequency of the respiratory distress syndrome or on perinatal mortality (King et al., 1988).

There is growing evidence that preterm labor is syndrome which can be induced by a variety of factors. Moreover, preterm labor has to be considered a chronic pathological condition of the uterus in response to a variety of etiological factors. In some clinical situations, decrease in progesterone levels or in progesterone action at the receptor level may result in preterm labor. In many species, preterm labor can be induced with progesterone antagonists (e.g., RU 486, onapristone) or progesterone synthase inhibitors (epostane, trilostane). There is growing evidence, however, that intrauterine or systemic infections play a key role in the etiology and pathogenesis of preterm labor in humans (for review see Romero et al.). In 20–40% of pre-term labor, there is clinical and/or biochemical evidence of the intrauterine infection such as hyperthermia, positive bacterial cultures, increase in cytokines such as IL-1b, TNFα, IL-8 in the amniotic fluid (Romero et al., 1991, 1992). It is well established that the cytokines are released from uterine macrophages, activated lymphocytes and other white blood cells in response to a lipopolysaccharide (LPS) which is a major constituent of outer bacterial membrane. The cytokines stimulate in turn the release of prostaglandins from the decidual and amnion cells which directly induce uterine contractions leading to preterm labor and subsequently to preterm birth.

Preterm birth associated with intrauterine infection is very resistant to conventional treatments (β-mimetics, antibiotics). There is no effective therapy for treatment of preterm birth associated with intrauterine infection to date.

Preeclampsia (toxemia) of pregnancy is characterized by a triad of hypertension, pathological edema and proteinuria. This disease, which affects 6 to 10% of all pregnancies, represents a significant health problem and is the leading cause of fetal growth retardation, fetal mortality and morbidity, premature birth and maternal mortality. The etiology of the disease is largely unknown and effective therapy is not available.

Epidemiological data indicate that approximately one half of the deaths in economically developed countries are attributable to a single major cause, viz., cardiovascular disease, including coronary heart disease, stroke and other forms of vascular disease (Green, A., Bain, C., 1993). The commonest and most lethal form of cardiovascular disease is coronary heart disease. In men, there is a continuous increase in the prevalence of cardiovascular disease after the age of 30–40 years. On the other hand, the rate of cardiovascular disease, especially coronary heart disease, is relatively low among premenopausal women but rises sharply with increasing age, suggesting that sex steroids (estrogens and progesterone) have a protective effect in women. The increased risk of coronary heart disease among women with bilateral oophorectomy further supports the view that steroid hormones may play a protective role with regard to cardiovascular disease.

Cardiovascular disease can be prevented in postmenopausal women by hormone replacement therapy (HRT) with estrogens. The recently performed meta-analysis of 29 studies has demonstrated a reduced cardiovascular disease risk among estrogen users in 23 of these studies (Stampfer et al., 1991). There is also experimental evidence from studies in monkeys that the development of coronary atherosclerosis induced by oophorectomy and diet may be reversed by estrogen supplementation (Adams et al., 1992). On the other hand, there are no effective methods for the prevention of cardiovascular disease in men, since estrogen cannot be used because of side-effects.

The mechanism of the protective effect of female sex hormones is not fully understood. An impact on the lipid profile may be possible. Among postmenopausal women, estrogens reverse the atherogenic changes in lipid profile which is associated with early menopause such as the increase in LDL-cholesterol and serum triglyceride levels and the decrease in HDL-cholesterol. However, new data suggest that both estrogens and progesterone may have a direct effect on the blood vessels. The presence of estrogen and progesterone receptors in arterial endothelial and smooth muscle cells supports the view that sex steroids may have a direct effect on the blood vessels (Lin et al., 1986). It has also been demonstrated that estrogen treatment results in the redistribution of arterial estrogen receptors and in the increase in arterial progesterone receptors in baboons (Lin et al, 1986). Monkey studies suggest that estrogens may prevent ovariectomy-induced atherosclerosis by inhibiting the uptake and degradation of LDL in the arterial wall (Adams et al., 1992). The effects of estrogens and/or progesterone on arterial tone may also explain some of the beneficial effects of HRT on arterial disease risk. From animal models it is known that estrogens increase uterine blood flow by regulating the vascular tone (Greiss & Anderson, 1970, Ganger et al., 1993). The effects of a sex steroid on the vascular tone suggest that sex steroids may play a role in the pathogenesis of hypertension.

The effects of steroids on the vessels can be mediated by various locally produced hormones including nitric oxide (NO), prostacyclin and endothelin. Both nitric oxide and prostacyclin induce vascular relaxation and inhibit platelet aggregation. On the other hand, endothelin has a strong vasoconstriction effect. Nitric oxide is produced by endothelial cells and is involved in the regulation of vascular tone, platelet aggregation, neurotransmission and immune activation (Furchgott and Zawadzki, 1980; Moncada, Palmer and Higgs, 1991 ). Nitric oxide, formerly known as EDRF (endothelin-derived relaxing factor) (Furchgott and Zawadzki, 1980; Moncada, Palmer and Higgs, 1991 ), is synthesized by the oxidative deamination of a guanidino nitrogen of L-arginine by at least three different isoforms of a flavin-containing enzyme, nitric oxide synthase (Moncada, Palmer and Higgs, 1991). Nitric oxide elevates levels of cGMP (1,3,5-cyclic guanosine monophosphate) within the vascular smooth muscle to produce relaxation and to reduce blood vessels tone (Moncada, Palmer and Higgs, 1991).

Preeclampsia is often considered as an acute form of atherosclerosis. The spiral arteries that perfuse the intervillous space of normal placenta undergo extensive morphological changes during normal pregnancy, viz., a fourfold increase in diameter and a loss of their muscular and elastic components (Robertson 1986). These changes allow for an approximate tenfold increase in uterine blood flow that occurs during normal gestation. These changes are absent in preeclampsia (Robertson 1986) so that the intramyometrial segments of the spiral arteries are unable to dilate. In addition, the basal arteries and myometrial segments of spiral arteries in the preeclamptic placenta demonstrate characteristic lesions which have been called "acute atherosis" (Roberts 1989). In acute atherosis of the preeclampsia uterus there is an endothelial cell injury, a focal interruption of the basement membrane, platelet deposition lipoid necrosis of muscle cells (foam cells), (a result of chronic hypoxia and/or cytotoxins), mural thrombi and fibrinoid necrosis (Robertson 1967, DeWolf 1980, Roberts 1989), effects very similar to those seen in atherosclerotic vascular disease.

Endothelins are a family of small proteins which were originally isolated from cultured endothelial cells. Endothelin is a vasoactive peptide composed of 21 amino acid residues. Endothelin was isolated from the culture supernatant of the endothelial cells of porcine aortas. Its structure was determined by M. Yanagisawa in 1988. More recently, research on the gene coding for endothelin revealed the presence of peptides similar to endothelin in structure.

These peptides are named endothelin-1 (ET-1), endothelin-2 (ET-2), and endothelin-3 (ET-3). These 21-residue peptides are formed from a preproendothelin (200 residues) by way of 38/39-residue intermediate (proendothelins). Preproendothelin-1 is cleaved by dibasic-pair specific endoproteases to form proendothelin-1, a 38-amino acid precursor peptide. Proendothelin-1 is cleaved by the action of an "endothelin-converting enzyme" (ECE). Several endopeptidases, including metalloendopeptidase sensitive to phosphoramidon and the endopeptidase-2.4.11 sensitive to SQ 28 608 are also involved in converting proendothelin-1 to form endothelin 1 (Haynes and Webb, (1993).

Peptides of the endothelin family show vasopressor activity in vitro and in vivo. In addition to their effects on vascular contractility, ET-1 is one of the most potent stimulators of uterine contractility. In vitro experiments with rat and rabbit uterine tissue have demonstrated strong, dose-dependent uterotonic activity of ET-1. The ET-1 induced uterine contractions were similar to those induced with oxytocin and were inhibited with calcium channel antagonists (Kozuka et al., 1989; Calixto & Rae, 1991; Suzuki, 1991).

In the rabbit, specific immunostaining of ET-1 has been observed in the endometrium but not in the myometrium, whereas the specific ET-1 receptors have been found only in the myometrium (Maggi et al., 1991). These findings are suggestive of a paracrine action of ET-1. These studies also indicate that endothelin receptor density on myometrial cells is controlled by the steroid hormones (i.e., estrogen stimulates receptor number and progesterone counteracts this action). It has been suggested that ET-1 levels in maternal plasma increase during labor; however, Mitchell et al. (1991) and Romero et al. (1992) have demonstrated that ET-1 and ET-2 levels do not increase with labor at term or preterm in the absence of infection.

It has recently been found that ET-1 is produced in relatively high amounts in human endometrium, predominantly in the stromal cells (Economos et al., 1992). The highest concentrations of ET-1 in the human endometrium have been found at the time of menstruation (Ohbuchi et al., 1992). Receptors for ET-1, ET-2 and ET-3 have been identified in the human glandular epithelium and spiral arteries (Davenport et al., 1991). The exact mechanism of menstruation is not fully understood. In the uterus, endothelins are degraded by enkephalinases. The enkephalinases (membrane metalloendopeptidases, MMEP) catalyze the degradation of small bioactive peptides such as endothelins, enkephalins, atrial natriuretic factor, substance P, and others. It has been found that the endometrial enkephalinase is a progesterone-dependent protein. It correlates with plasma progesterone levels, in a highly significant manner (MacDonald et al., 1991; Casey et al., 1992). It has been suggested that the decrease in endometrial enkephalinase at the time of luteolysis together with the increase in the synthesis of ET-1 by stromal cells may result in the increase in the local concentration of ET-1 and in turn in menstruation (Casey et al., 1992). Thus, the ET-1/enkephalinase-system in the endometrium was suggested to play a role in the onset of menstruation in humans (MacDonald et al., 1991). Since enkephalinases in the uterus seem to be regulated by the steroid hormones, especially progesterone, it is possible that enkephalinases in vascular tissues are similarly controlled and that during pregnancy, when steroid hormone levels are elevated, there is some function of vascular enkephalinases to maintain blood flow. Therefore, the endothelin-mediated mechanisms controlling both the onset of labor and menstruation may be similar.

Five different sequences of endothelin receptors have been reported. The receptors from 2 different receptor subtypes, A and B, which can be distinguished by their affinities for the various endothelins. The endothelin A receptor ($ET_A$-R) has a greater affinity for the ET-1 and ET-2 than for ET-3, while the B-subtype is non-specific.

The cyclo(D-Trp.D-Asp.Pro.D-Val.Leu) which called BQ-123 has first been reported as a selective $ET_A$ receptor antagonist by K. Ishikawa et al., in 1991 (Proc. 12th Am. Peptid- Symp. Abst. P506). The manufacture and the structure of this antagonist is described in R. A. Atkinson and J. P. Pelton, (1992). Biological effects of BQ-123 were reported by K. Nakamichi et al., (1992).

PD 142 893 is an example for a non-selective ET antagonist which binds to both $ET_A$-R and $ET_B$-R (Warner et al., 1993).

Ro 46-2005 is a non-specific, non-peptidic, orally active ET-antagonist which efficacy was demonstrated in various animal models (prevention of post-ischemic renal vasoconstriction in rats, prevention of the decrease in cerebral blood flow after subarachnoid hemorrhage in rats and lowering of blood pressure in sodium-depleted squirrel monkeys). Clozel et al., (1993).

Other ET-antagonists include BMS 182847 [5-(dimethyl-amino)-N-(3,4-dimethyl-5-isoxazolyl)-1--naphthalene-sulphonamide], a highly selective $ET_A$ orally-active antagonist; SB 209670 [(+)-1S,2R,S-3-(2-carboxymethoxy-4methoxyphenyl)-1-(3,4-methylenedioxyphenyl)-5-(prop-1-yloxy)indane-2-carboxylic acid; and bosentan, disclosed, e.g., in S. A. Douglas et al., (1994).

SUMMARY OF THE INVENTION

The present invention provides a method for the prevention and treatment of preterm labor, imminent abortion, dysmenorrhea and menstrual disorders (i.e., dysfunctional uterine bleeding, menorrhagia, breakthrough bleeding) with an endothelin antagonist and/or an endothelin synthase (ECE) inhibitor.

In addition, the invention provides a method in which a progestational agent (progestin), a cyclooxygenase inhibitor and/or a nitric oxide (NO) donor and/or NO substrate is used in combination with an endothelin antagonist and/or an endothelin synthase inhibitor for the prevention and treatment of preterm labor, imminent abortion, dysmenorrhea and menstrual disorder (i.e., dysfunctional uterine bleeding, menorrhagia, breakthrough bleeding).

This invention further provides a method for the prevention and treatment of preeclampsia of pregnancy with an endothelin antagonist and/or an endothelin synthase inhibitor.

This invention also provides a method for the prevention and treatment of preecpampsia of pregnancy with an endothelin antagonist and/or an endothelin synthase inhibitor in combination with one or more of a progestin, a cyclooxygenase inhibitor, and/or an NO donor and/or NO substrate.

Still other aspects of the invention provide methods for the prevention and treatment of atherosclerotic vascular disease and hypertension in males and females with a combination of an endothelin antagonist and/or endothelin synthase inhibitor with steroid hormones (with an estrogen or with a combination of an estrogen and a progestin for females; with a progestin for males), and/or with an NO donor and/or NO substrate, and optionally with a cyclooxygenase inhibitor.

Yet another object of the invention is to provide hormone replacement therapy for peri- and post-menopausal females in need of such treatment with a combination of an endothelin antagonist and/or endothelin synthase inhibitor with steroid hormones (an estrogen or a combination of an estrogen and a progestin), and/or with a NO donor and/or NO substrate, and, optionally, with a cyclooxygenase inhibitor.

A further object is the provision of pharmaceutical compositions useful in practicing the methods of this invention.

Upon further study of the specification and appended claims, further objects and advantages of this invention will become apparent to those skilled in the art.

BRIEF DESCRIPTION OF THE DRAWINGS

Various other objects, features and attendant advantages of the present invention will be more fully appreciated as the same becomes better understood when considered in conjunction with the accompanying drawings, wherein:

FIG. 1, right side, demonstrates the effects of BQ-123 on fetal outcome in guinea pigs. The fetal mortality rate in the LPS-treated group was 100%. Treatment with BQ-123 reduced the fetal mortality (to 50%). All fetuses delivered at term have survived. The general condition of mother animals treated with BQ-123 plus LPS was better than those treated with LPS alone (subjective assessment of the technician).

DETAILED DESCRIPTION OF THE INVENTION

Figure 1:
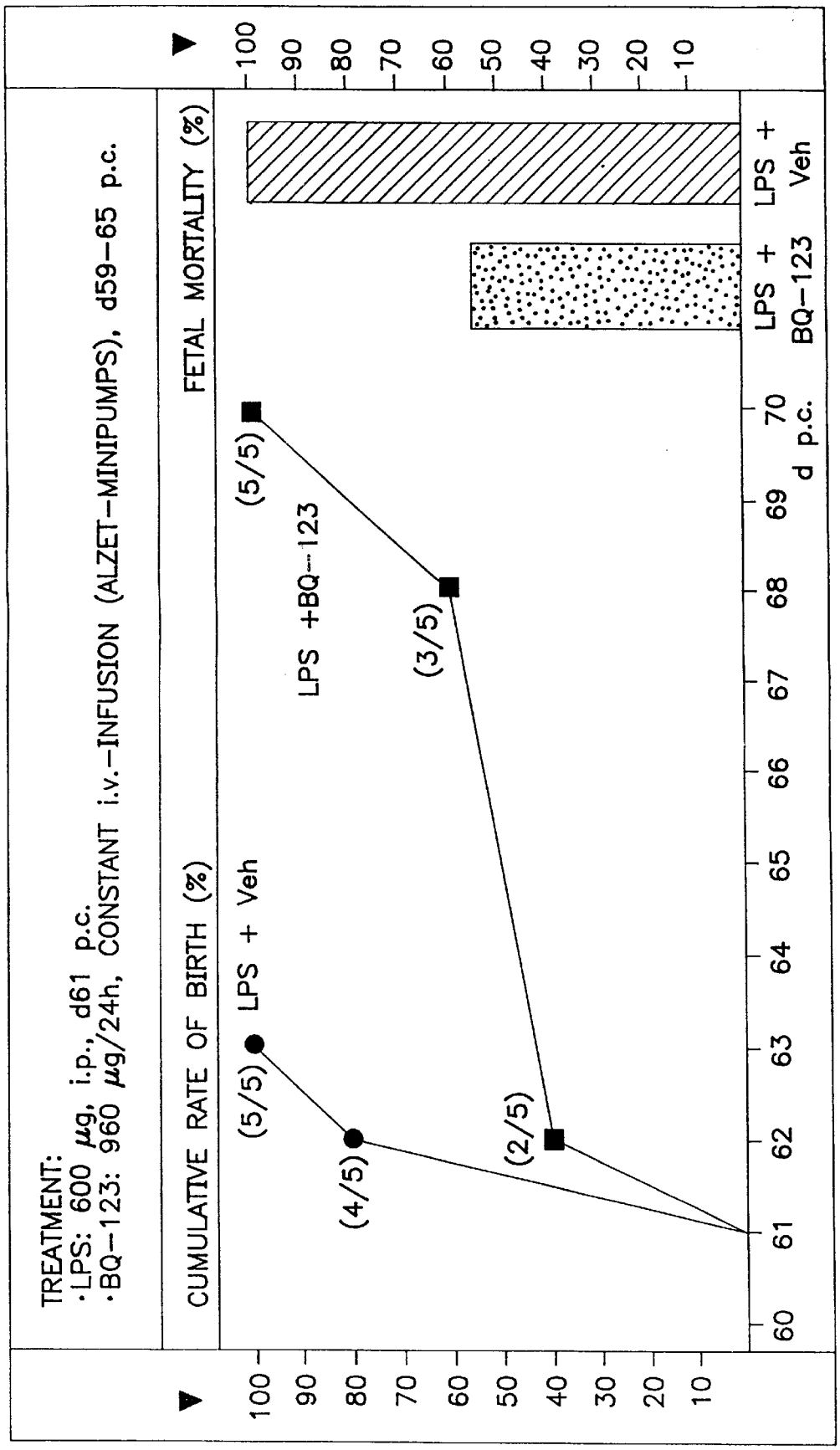
FIG. 1, left side, shows the inhibitory effects of the endothelin antagonist BQ-123 on preterm deliveries induced with the lipopolysaccharide LPS in late pregnant guinea pigs. The LPS is a non-specific labor-inducing agent which mimics preterm labor associated with an intrauterine infection (model of preterm birth). In the LPS-treated group, all animals delivered within 48 hours. Treatment with BQ-123 resulted in a partial inhibition (60%) of the LPS-induced preterm birth and reduced the fetal mortality (to 50%).

In a method aspect, this invention relates to a method of treating at least one of dysmenorrhea or other menstrual problems (e.g., dysfunctional uterine bleeding) in a non-pregnant female which comprises administering to a non-pregnant cycling female manifesting the symptoms thereof (a) one or both of an endothelin antagonist and an endothelin synthase inhibitor, and, optionally, (b) one or more of a progestin and/or a cyclooxygenase inhibitor, and, optionally, (c) one or more of a nitric oxide (NO) donor and/or NO substrate, in amounts effective to ameliorate the symptoms thereof, the amount of the progestational agent administered being bioequivalent to 50–300 mg of injected progesterone and the amount of the endothelin antagonist, endothelin synthase inhibitor or both being effective to block endothelin action at the receptor level or inhibit the endothelin synthesis, respectively.

In another method aspect, this invention relates to a method of treating preterm labor in a pregnant female which comprises administering to a pregnant female manifesting the symptoms thereof, amounts of (a) one or both of an endothelin antagonist and/or an endothelin synthase inhibitor to inhibit preterm labor, and (b) optionally, one of a progestin and/or a cyclooxygenase inhibitor, and, optionally, (c) one or more of a nitric oxide (NO) donor and/or NO substrate, the amount of the progestational agent administered being bioequivalent to 50–300 mg of injected progesterone and the amount of the endothelin antagonist; endothelin synthase inhibitor or both being effective to, respectively, either raise the blood level of circulating endothelin in a pregnant female to whom the composition is administered or to block endothelin receptor, and the amount of the cyclooxygenase inhibitor being bioequivalent to 10–2000 mg/day.

In another method aspect, this invention relates to a method of treating preeclampsia in a pregnant female which comprises administering to a pregnant female manifesting the symptoms thereof, amounts of (a) at least one of an endothelin antagonist and/or an endothelin synthase inhibitor to prevent preeclampsia, and, optionally, (b) one or more of a progestin and/or a cyclooxygenase inhibitor, and, optionally, (c) one or more of a nitric oxide (NO) donor and/or NO substrate, at dosage ranges as described above.

In another method aspect, this invention relates to a method of treating or preventing atherosclerotic vascular disease which comprises administering to a male or female in need of such treatment, (a) one or both of an endothelin antagonist and/or an endothelin synthase inhibitor in combination with (b) one or more of a progestin (for males) and/or estrogen (for females), and/or one or more of a nitric oxide (NO) donor and/or NO substrate, and, optionally, (c) a cyclooxygenase inhibitor, in amounts effective to ameliorate the symptoms thereof, the amount of the progestational agent administered being bioequivalent to 50–300 mg of injected progesterone, the amount of estrogenic agent administered being a daily dose bioequivalent to about 1–2 mg/day of estrogen, and the amount of the endothelin antagonist, endothelin synthase inhibitor or both being effective to block endothelin action at the receptor level or to inhibit endothelin synthesis by at least 20%, respectively.

In yet another method aspect, this invention relates to a method of treating or preventing hypertension which comprises administering to a male or female in need of such treatment, (a) one or both of an endothelin antagonist and/or an endothelin synthase inhibitor in combination with (b) a progestin (for males), and/or estrogen (for females), and/or one or more of a nitric oxide (NO) donor and/or NO substrate, and, optionally, (c) a cyclooxygenase inhibitor, in amounts effective to ameliorate the symptoms thereof, the amount of the progestational agent administered being bioequivalent to 50–300 mg of injected progesterone, the amount of estrogenic agent being a daily dose bioequivalent to about 1–2 mg/day of estrogen, and the amount of the endothelin antagonist, endothelin synthase inhibitor or both being effective to block endothelin action at the receptor level or to inhibit the endothelin synthesis by at least 20%, respectively.

In still another method aspect, this invention relates to a method of providing hormone replacement therapy to a perior post-menopausal female in need of such treatment, e.g., a female who is, because of disease, surgery or age, not producing a sufficient amount of female hormones to maintain health or comfort, which comprises administering (a) one or both of an endothelin antagonist andor an endothelin synthase inhibitor in combination with (b) a progestin, and/or one or more of a nitric oxide (NO) donor and/or NO substrate, and, optionally, (c) a cyclooxygenase inhibitor, in amounts effective to ameliorate the symptoms thereof, the amount of the progestational agent administered being bioequivalent to 50–300 mg of injected progesterone, the amount of estrogenic agent being a daily dose bioequivalent to about 1–2 mg/day of estrogen, and the amount of the endothelin antagonist, endothelin synthase inhibitor or both being effective to block endothelin action at the receptor level or to inhibit the endothelin synthesis by at least 20%, respectively.

In one product aspect, this invention relates to a pharmaceutical composition consisting of (a) an endothelin antagonist and/or endothelin synthase inhibitor, in combination with at least one of (b) a progestin, (c) an estrogen, (d) a cyclooxygenase inhibitor, (e) a nitric oxide (NO) donor and/or (f) an NO substrate, with the amount of the endothelin antagonist being equivalent to that needed to block 80% of the endothelin receptor; the amount of endothelin synthase inhibitor being equivalent to that amount needed to lower blood levels of endothelin by at least 20%, preferably 50%; the of progestational agent per unit dosage being bioequivalent to 50–300 mg of injected progesterone; the estrogenic agent per dosage unit being bioequivalent to about 1–2 mg/day of estrogen, the cyclooxygenase inhibitor being bioequivalent to 10–2000 mg of aspirin; the NO donor being bioequivalent to that amount needed to raise NO at the target site by >20%, preferably 50%; and/or the amount of NO substrates being bioequivalent to 100–10,000 mg/day of L-arginine.

In another product aspect, this invention relates to a pharmaceutical composition consisting of an endothelin antagonist and/or endothelin synthase inhibitor, and one or both of an estrogen and a progestin, and/or one or more of a nitric oxide (NO) donor and/or NO substrate, and, optionally, (c) a cyclooxygenase inhibitor, with the amount of the endothelin antagonist being equivalent to that needed to block 80% of the endothelin receptor, and the endothelin synthase inhibitors needed to lower blood levels of endothelin by at least 20%, preferably 50%; the progestational agent per unit dosage being bioequivalent to 50–300 mg of injected progesterone; the estrogenic agent being bioequivalent to about 1–2 mg/day of estrogen;, the amount of NO donor bioequivalent to that amount needed to raise NO at the target site by >20%, preferably 50%; the amount of NO substrate bioequivalent to 100–10,000 mg/day of L-arginine; and the amount of cyclooxygenase inhibitor bioequivalent to 10–2000 mg of aspirin.

The present invention provides pharmaceutical compositions and methods of treatment for menstrual disorders, e.g. dysmenorrhea, in a non-pregnant mammal, or preterm labor, imminent abortion, and/or preeclampsia in a pregnant mammal, preferably a human, who is manifesting the symptoms thereof or who is a high risk candidate for doing so, e.g., as determined by the progress of a present or previous pregnancy. In addition, the invention provides pharmaceutical compositions and methods for treating atherosclerotic vascular disease, hypertension, and hormone replacement therapy (HRT) in a female mammal, preferably a human, and in the latter case, a female, who is manifesting the symptoms thereof (atherosclerotic vascular disease or hypertension) or in need thereof (HRT).

Because these abnormal conditions are produced or aggravated by supranormal levels of endothelin synthesis or activity, endothelin antagonists and/or endothelin synthase inhibitors are useful for ameliorating the symptoms thereof and, in one aspect of the method of this invention, a combination of both can be employed. In addition, since progestins and cyclooxygenase inhibitors, respectively, control the synthesis, metabolism or activity of endothelin, a combination of one or more of these compounds with one or more of an endothelin antagonist and/or endothelin synthase inhibitor will be particularly useful for the above abnormal conditions. Still further, for the treatment of atherosclerotic vascular disease and hypertension, a combination of one or more of an endothelin antagonist and/or endothelin synthase inhibitor with a progestin (in the case of males) or an estrogen or a combination of an estrogen and a progestin (in the case of females) is particularly useful; the latter combinations are also useful for female hormone replacement therapy. In the latter cases, the combination of an endothelin antagonist in combination with a progestin has surprisingly provided synergistic effects. Still further combinations can include NO donors and/or NO substrates, which increase the amount of nitric oxide, thereby inducing vascular relaxation, and which can replace the steroid hormones.

Thus, the method and pharmaceutical composition aspects of this invention employ (a) an endothelin antagonist (e.g., BQ-123, PD 142 893, Ro 46-2005, BMS 182874, SB 209670, bosentan) and/or an endothelin synthase inhibitor (e.g., phosphoramidon or SQ 28 608) and optionally (in the case of menstrual disorders, preterm labor, preeclampsia or fetal growth retardation) (b) one or more of a progestin (e.g., progesterone, levonorgestrel, desogestrel, gestodene), a cyclooxygenase inhibitor (e.g., aspirin, indomethacin), an NO donor (e.g., nitroglycerin, sodium nitroprusside, SIN-1, isosorbid mono- or dinitrate) and/or an NO substrate (e.g., L-arginine). In the case of treating atherosclerotic vascular disease, hypertension and for hormone replacement therapy, components (a) and (c) are employed, wherein (c) is a progestin, (or, when a female is being treated, an estrogen or a combination of a progestin and an estrogen), and/or a nitric oxide donor and/or a nitric oxide substrate, and, optionally, a cyclooxygenase inhibitor. In particular, cobminations of an endothelin antagonist with and NO donor or NO substrate are preferred.

Examples of combinations of active agents which can be administered concurrently with an endothelin antagonist and/or endothelin synthase inhibitor are a progestin (progesterone) and/or a cyclooxygenase inhibitor (aspirin), and/or an NO donor (nitroglycerin) or substrate (L-arginine).

Endothelin antagonists and endothelin synthase inhibitors: Examples of dosage ranges of typical endothelin antagonists and endothelin synthase inhibitors are:

| Endothelin Antagonist | Dosage, mg/day/50 kg | Dosage, mg/kg |
|---|---|---|
| BQ-123 | 1–2000, s.c. | 1–40, s.c., i.m., i.v. |
| PD 142 893 | Dose effective to block 50% of receptors | |
| Ro 46-2005 | 50–5000, p.o. | 0.1–100, p.o. |
| SB 209670 | 1–100, p.o. | 0.01–20, p.o. |
| BMS 182874 | 1–100, p.o. | 0.01–20, p.o. |
| bosentan | 1–100, p.o. | 0.01–20, p.o. |

| Endothelin Synthase Inhibitor | Dosage |
|---|---|
| phosphoramidon | Dose effective to reduce endothelin levels by > 20% |
| SQ 28 608 | |

The following are typical oral dosage ranges, active agents of the progestin and the optional other active agents concurrently administered with the endothelin antagonist and/or endothelin synthase inhibitor:

Progestins: A daily dose bioequivalent to 50–300 mg of progesterone/day, e.g., an injectable suspension of medroxyprogesterone acetate to provide a weekly dose thereof of 100–1000 mg; tablets or dragees providing an oral dose thereof of 5–10 mg/day; an injectable solution of hydroxyprogesterone caproate which provides a weekly dose of 250–500 mg; tablets, capsules or dragees of norethindrone acetate which provide a daily dose of 5–20 mg.

Daily doses of progestogens taken for 12 days/month in patients receiving oral or transdermal estrogens:

| Progestin | Dosage |
|---|---|
| Noresthisterone | 0.7–2.5 mg/day |
| Medroxyprogesterone acetate | 10 mg/day |
| Norgestrel | 150 μg/day |
| Dydrogesterone | 10–20 mg/day |

Estrogens and estrogens plus progestins: Estrogens and estrogens plus progestins can be administered at dosages typically used for contraception and hormone replacement therapy. Examples of suitable estrogens and dosages thereof include a daily dose bioequivalent to about 1–2 mg/day of estrogen, e.g., Prermarin®, Wyeth-Ayerst, 0.625 mg/day; estradiol valerate, 50 μg/day transdermally; vaginal estadiol creams, 1.25 mg/day; and vaginal estradiol rings, 0.2 mg/day, as well as the naturally occurring estrogens used in hormone replacement therapy currently available, e.g., in the U.K.

Examples of estrogens and estrogen plus progestin combinations include:

| Product | Composition | Dase, mg/day |
|---|---|---|
| Climoval ® (Sandoz) | Estradiol valerate | 1 or 2 |
| Progynova ® | Estradiol valerate | 1 or 2 |
| Harmogen ® (Abbott) | Piperazine estrone sulfate | 1.5 or 2.5 |
| Hormonin ® (Shire) | Estradiol + estrone + estriol | 0.6 |
| Premarin ® | Conjugated equine estrogens | 0.625, 1.25 or 2.5 |

Commercially available combination calender packs for hormone replacement therapy include "Estrapak", "Prempak-C", "Trisequens", "Trisequens forté" and "Cyclo-progynova". The following are illustrative compositions of such products:

Estradiol 50 mg/day (28 days, 8 patches)
Conjugated equine estrogens 0.0625 mg/day (28 days)
Estradiol valerate 2 mg/day (11 days)
Estradiol valerate 2 mg/day
Norgestrel 0.5 mg/day (10 days)
Norgestrel 0.15 mg/day (12 days)
Conjugated equine estrogens 1.25 mg/day (28 days)
Norgestrel 0.15 mg/day (12 days)
Estradiol 2 mg/day+estriol 1 mg/day (22 days)
Norethisterone acetate 1 mg/day (10 days)
Estradiol 1 mg/day+estriol 0.5 mg/day (6 days)
Estradiol 4 mg/day+estriol 1 mg/day (21 days)
Norethisterone acetate 1 mg/day (10 days)
Estradiol 1 mg/day+estriol 0.5 mg/day (6 days)
Estradiol valerate 1 mg/day (21 days)
Levonorgestrel 0.25 mg/day (10 days)
Estradiol valerate 2 mg/day (21 days)
Levonorgestrel 0.5 mg/day (10 days)

Cyclooxygenase Inhibitors: Aspirin can be used at a dosage of 10–2000 mg/kg/day p.o. Other suitable cyclooxygenase inhibitors include both COX-1 and COX-2 inhibitors, including, e.g., indomethacin; and dexamethasone, 6-(2,3-difluorophenoxy)-5-methylsulfonylamino-1-indanone (ZK 38.997, CGP 28 238 or Flosulide), 5-methylsulfonylamino-6-phenoxy-1-indanone (CGP 28 237), an dvarious 1,2-diarylcyclopentenes (e.g., as disclosed in Reitz et al., 1994) (COX-2 inhibitors). Each of these can be administered in conventional, or lower, dosages. In particular, preferred cyclooxygenase inhibitors are those which are specific COX-2 inhibitors, such as those disclosed in Böttcher et al., Wiesenberg-Böttcher, Reitz et al., Zimmerli et al., and Mitchell et al.

Nitric oxide donors and/or substrates: Suitable nitric oxide donors and substrates can be selected from the well known anti-angina agents; see, e.g., "Nitrates and other Anti-angina Agents" in Martindale: The Extra Pharmacopoeia, (1993); exemplary agents and suitable dosages for each, are listed below:

| Dosage | |
|---|---|
| Nitric Acid Donor | |
| Nitroglycerin | 2.5 mg twice daily p.o. |
| | 0.8 mg 1–4 times daily, sublingual |
| | 0.2–0.4 mg/hr transdermal patch |
| Sodium nitroprusside | 500–2000 µg/kg/day |
| SIN-1 | Dosage effective to raise NO at |
| Isosorbid mono- or dinitrate | target site > 20% |
| Nitric Acid Substitute | |
| L-arginine | 100–10,000 mg/day i.m., i.v., p.o. |

The pharmacologically active agents employed in this invention can be administered in admixture with conventional excipients, i.e., pharmaceutically acceptable liquid, semi-liquid or solid organic or inorganic carriers suitable, e.g., for parenteral or enteral application and which do not deleteriously react with the active compound in admixture therewith. Suitable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethyl cellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

In a preferred aspect, the composition of this invention is adapted for oral ingestion. For enteral application, particularly suitable are unit dosage forms, e.g., tablets, dragees or capsules having talc and/or a carbohydrate carrier or binder or the like, the carrier preferably being lactose and/or corn starch and/or potato starch; particulate solids, e.g., granules; and liquids and semi-liquids, e.g., syrups and elixirs or the like, wherein a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions. Each unit dose, e.g., each tablespoon of liquid or each tablet, or dragee contains, for example, 5–5000 mg of each active agent. Solutions for parenteral administration contain, for example, 0.1–1% of each active agent in an aqueous or alcoholic solution.

The endothelin antagonist and/or endothelin synthase inhibitor can be administered as an admixture with the progestational agent and any other optional active agent or as a separate unit dosage form, either simultaneously therewith or at different times during the day from each other.

RESULTS

FIG. 1 demonstrates for the first time the efficacy of an endothelin antagonist in the treatment (prevention) of preterm birth. The LPS-dose used in this study (600 µ/animal) was very high, while is consistently induced 100% abortion in both mid-pregnant (day 42–43 p.c.) and late-pregnant (day 60 p.c.) guinea pigs in previous studies. This explains why the effects of BQ-123 were only partial.

Preterm birth associated with intrauterine infection is very resistant to conventional treatments (β-mimetics, antibiotics), and there is no effective therapy for treatment of preterm birth associated with intrauterine infection to date. This study indicates that endothelin antagonists or endothelin synthase inhibitors can be used for prevention and/or treatment of preterm birth, in particular preterm birth associated with intrauterine infection. In non-pregnant women, dysmenorrhea is also associated with an increased uterine activity. These results indicate that endothelin antagonists and/or endothelin synthase inhibitors may be effective in the treatment of uterine contractility in non-pregnant women.

Figure 2:
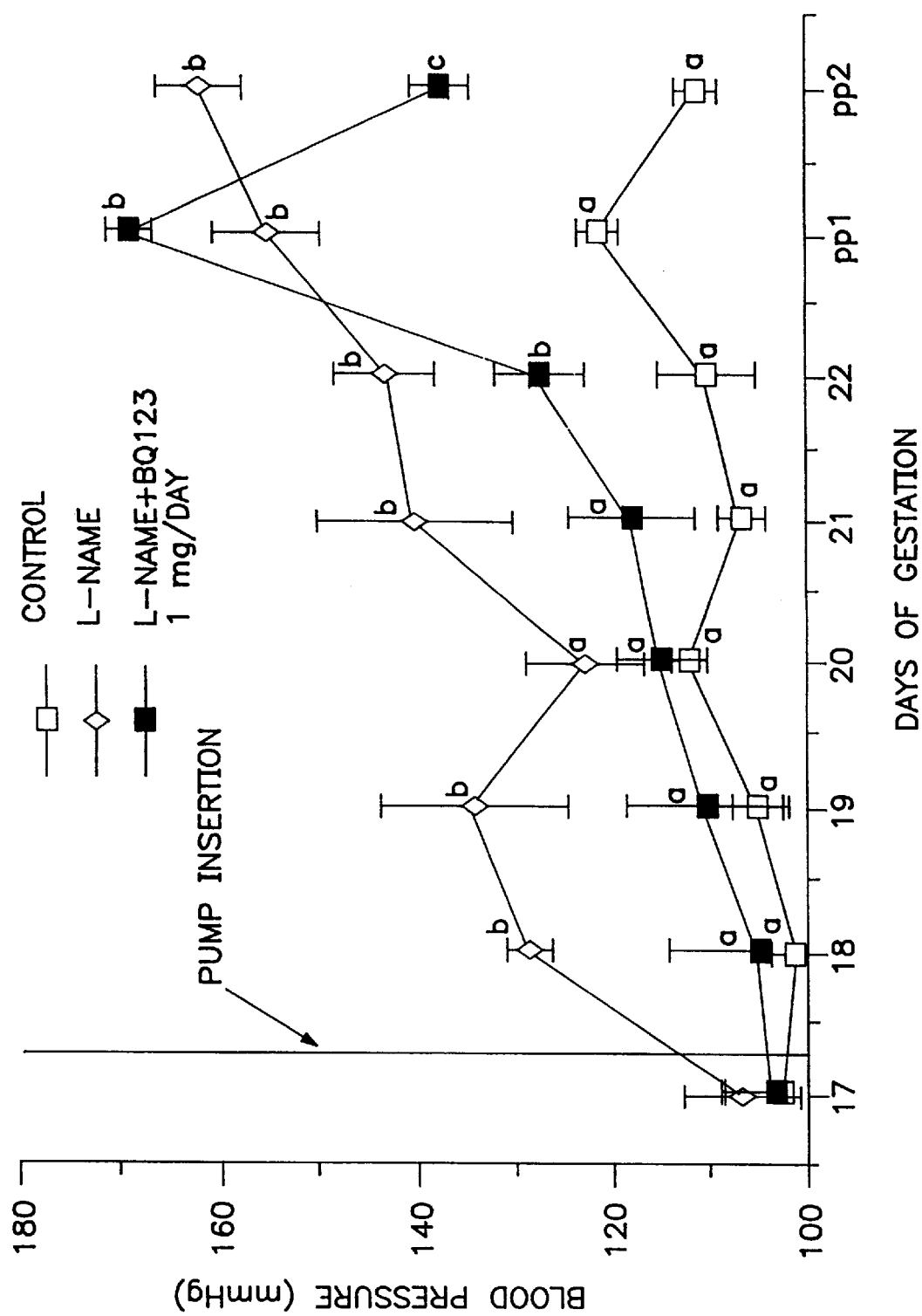
FIG. 2 shows the effect of BQ-123 on L-NAME (nitric oxide synthase inhibitor)-induced hypertension in pregnant rats (preeclampsia model). BQ-123 significantly lowered the blood pressure (BP) in animals treated with L-NAME compared to rats treated only with L-NAME.
Figure 3:
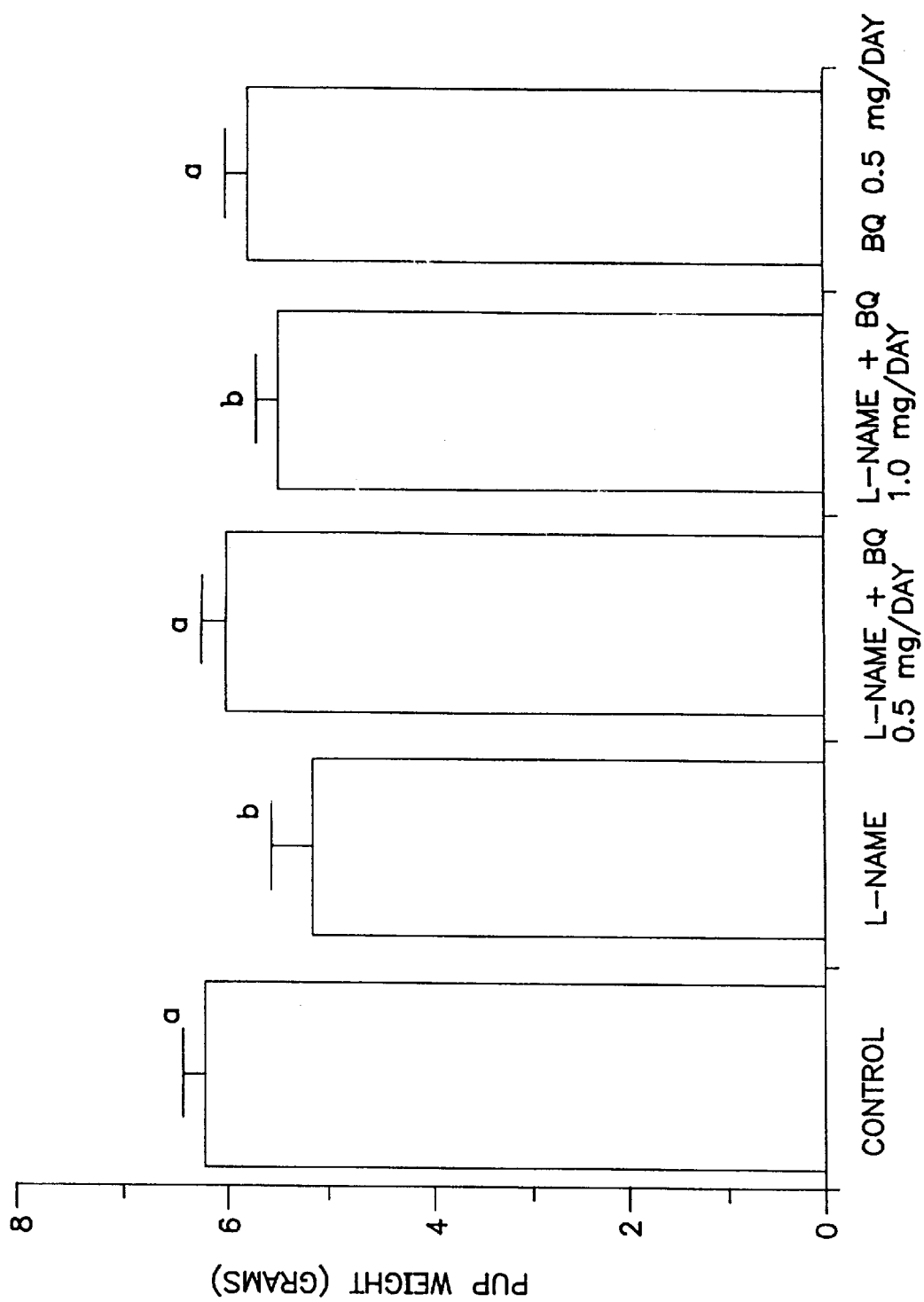
FIG. 3 shows the fetal weights in control rates and in pups delivered following treatment with L-NAME with and without BQ-123. The pup weight was significantly smaller after L-NAME treatment. However, the pup weight was similar to control pups in animals treated with L-NAME plus BQ-123.

The results shown in FIGS. 2 and 3 show that BQ-123 effectively reduces the blood pressure and fetal weights in pregnant preeclamptic rats (L-NAME-treated). This is the first demonstration of a reversibility of preeclampsia symptoms (BP and fetal growth retardation) with an endothelin antagonist. It can be concluded from these studies that endothelin antagonists and/or endothelin synthase inhibitors will be useful for the treatment of preeclampsia or other forms of fetal growth retardation (e.g., renal disease, placental hypoperfusion).

The BP-lowering effect of BQ-123 is greatly attenuated postpartum where progesterone levels drop, so that pregnancy (progesterone) is essential for its effectiveness. This observation indicates that an endothelin antagonist acts synergistically with progesterone.

The method of treatment employed in this invention can also be employed for the treatment of hypertension in both females (in combination with estrogen and/or progestin) and males (in combination with progestin), hormone replacement therapy for climacteric disorders (hot flushes, mood swings) in peri- and post-menopausal women (in combination with estrogen or estrogen and progestin), atherosclerotic vascular disease in females (in combination with estrogen and/or progestin) and males (in combination with progestin), thrombotic disorders, and hemorrhage, etc., following the dosage regimen described herein.

Screening tests for compounds and compositions having effectiveness for treating preeclampsia, gestational hypertension and fetal growth retardation can be conducted essentially as described in C. Yallampalli et al., (1993). This method involves administration of varying amounts of L-nitro-arginine methyl ester (L-NAME), a nitric oxide synthesis inhibitor, to pregnant rats. For example, lower amounts (10–25 mg/day/rat) of L-NAME induce only gestational hypertension, while higher amounts (50 mg/day/rat) also induced preeclampsia and/or fetal growth retardation.

Screening tests for compounds and compositions having effectiveness for treating preeclampsia and preterm birth can be conducted essentially as described in Bukowski et al., (1993); and Garfield et al., (1994). This methods include administration of varying amounts of L-nitro-arginine methyl ester (L-NAME), a nitric oxide synthesis inhibitor, to pregnant guinea pigs. For example, lower amounts (lower than 10 mg/day/animal) of L-NAME induce only preeclampsia while higher amounts (10–25 mg/day/animal) also induced preterm labor.

Other screening tests for compounds and compositions having effectiveness for such treatments, particularly preterm birth caused by bacterial infections, especially by Gram-negative bacteria, are disclosed in, e.g., Romero et al., (1992). This model uses lipopolysaccharide (LPS) induction of preterm labor in mice.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1
Treatment of Preterm Labor

To a pregnant human female (ca. 20 to 40 years; 60 to 80 kg) usually in her second half of pregnancy and displaying the symptoms of preterm labor, including uterine contraction, administer an endothelin antagonist (e.g., BQ-123) at a dosage of 1–2000 mg/day, s.c., or BMS 182874 at a dosage of 1–100 mg/kg, p.o., and optionally a progestin (e.g., 200 mg of micronized progesterone p.o. daily), and/or a cyclooxygenase inhibitor (e.g., aspirin, at a dosage of 10–2000 mg/day) until the symptoms are ameliorated.

Example 2
Treatment of Preterm Labor

To a pregnant human female comparable to the one described in Example 1, administer an endothelin synthase inhibitor (e.g., at a dosage effective to lower endothelin levels by >20% as compared with normal levels) and, optionally a progestin (e.g., 200 mg of micronized progesterone p.o. daily) or a cyclooxygenase inhibitor (e.g., aspirin at a dosage of 10–2000 mg, p.o.) to relieve the symptoms thereof.

Example 3
Treatment of Dysmenorrhea

To a non-pregnant human female (ca. 20 to 50 years, 60–80 kg) displaying the symptoms of dysmenorrhea or menstrual disorders, including painful uterine contractions, administer an endothelin antagonist (e.g., BQ-123 or BMS 182874) and optionally a progestin (e.g., 200 mg of micronized progesterone p.o. daily) and/or a cyclooxygenase inhibitor (e.g., aspirin, at a dosage of 10–2000 mg/day) to ameliorate the symptoms thereof.

Example 4
Treatment of Dysmenorrhea

To a non-pregnant female similar to the one in Example 3, administer an endothelin synthase inhibitor (e.g., phosphoramidon or SQ 28 608 at a dosage effective to lower endothelin levels by >20% as compared with normal levels) and optionally a progestin (e.g., 200 mg of micronized progesterone per os daily) and/or a cyclooxygenase inhibitor (e.g., aspirin, 10–2000 mg/day, p.o.) to relieve the symptoms.

Example 5
Treatment of Preeclampsia

To a pregnant human female (ca. 20 to 40 years 60 to 80 kg) usually in her second half of pregnancy displaying the symptoms of preeclampsia, including high block pressure, fetal retardation and proteinuria, administer an endothelin antagonist (e.g., BQ-123, 1–2000 mg/day, s.c.) and, optionally a progestin (e.g., 200 mg of micronized progesterone per os daily) and/or a cyclooxygenase inhibitor (e.g., aspirin, 10–2000 mg/day, p.o.) to ameliorate the symptoms.

Example 6
Treatment of Preeclampsia

To a pregnant female comparable to the one in Example 5, administer an endothelin synthase inhibitor and optionally a progestin and/or a cyclo-oxygenase inhibitor and/or a nitric oxide donor and/or nitric acid substrate to relieve the symptoms thereof, each as described above.

Example 7
Screening for Compounds having Effectiveness for Treating Preeclampsia. Gestational Hypertension and Fetal Growth Retardation Induction of preeclampsia in pregnant rats or guinea pigs on about day 16 of gestation in rats and approximately day 45 gestation in guinea pigs is effected with daily treatment with L-NAME. The L-NAME-treated animals are used to screen agents that lower blood pressure and increase fetal survival and prevent fetal growth retardation.

Example 8
Screening for Compounds having Effectiveness for Treating Preterm Labor Pregnant animals (rats or guinea pigs) are treated with an NO inhibitor (e.g., L-NAME), or an endothelin agonist (e.g., endothelin), with and without an antiprogestin or LPS to induce preterm labor, followed by treatment with agents to be screened for their ability to prevent preterm labor.

Example 9
Treatment of Atherosclerotic Vascular Disease

To human male or female (ca 45 years; 50–80 kg) displaying signs of cardiovascular disease, administer 1–100 mg/day/50 kg BMS 182874 at a dose of 0.01–20 mg/kg p.o., in combination with a progestin (e.g., 5–20 mg norethindrone acetate).

Example 10
Treatment of Hypertension

To human male or female (ca 45 years; 50–80 kg) displaying the signs of hypertension, administer 1–10 mg BMS 182874 p.o., in combination with a progestin (e.g., 5–20 mg norethindrone acetate).

Example 11
Hormone Replacement Therapy

To a non-pregnant human female (ca 45 years; 50–80 kg) displaying the signs of peri-menopause or postmenopausal symptoms administer 1–10 mg BMS 182874 p.o., in combination with either an estrogen only hormone replacement therapy or an estrogen plus progestin hormone replacement therapy.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

M. Yanagisawa et al., Nature 332:411–415 (1988).

Creasy R. K. (1989) Preterm labor and delivery. In Creasy R. F., Resnik., R. (eds.), Maternal-fetal medicine: Principles and practice. W. B. Saunders Company, Philadelphia, London, Toronto, Montreal, Sydney, Tokyo, pp. 477–505.

King J. F., Grant, A., Kierse, M. J. N., Chalmers, J. (1988) β-Mimetics in preterm labour; an overview of the randomized controlled trials. Brit. J. Obstet. Gynecol. 95:211–22.

Romero, R., Mazor, M., Wu, Y. K., Sirtori, M., Oyarzun, E., Mitchell M. D., Hobbins, J. C. (1988) Infection in the pathogenesis of preterm labor. Semin. Perinatol. 12:262–279.

Kozuka, M., Ito, T., Takahashi, K., Hagiwara, H. (1989) Endothelin induces two types of contractions of rat uterus: phasic contractions by way of voltage-dependent calcium channels and developing contractions through a second type of calcium channels. Biochem. Biochem. Res. Comm. 159(1):317–323.

Romero, R., Brody, D. T., Oyarzun, E., Mazor, M., Wu, Y. K., Hobbins, J. C., Durum, S. K. (1989) Infection and labor. III. lnterleukin-1: Signal for the onset of parturition. Am. J. Obstet. Gynecol. 160:117–123.

Romero, R., Ceska, M., Avila, C. A., Mazor, M., Behnke, E., Lindley, J. (1991) Neutrophil attractant/activating peptide-1/interleukin-8 in term and preterm parturition. Am. J. Obstet. Gynecol. 165:813–20.

Calixto, J. B., Rae, G. A. (1991) Effects of endothelins, Bay K 8644 and other oxytocics in non-pregnant and late pregnant rat isolated uterus. Eur. J. Pharmacol. 192(1):109–16.

C. Yallampalli et al., Am. J. Obstet. Gynecol. 169:1316–1320 (1993).

Zuzuki, Y. (1990) Properties of endothelin-induced contractions in the rabbit non-pregnant and pregnant myometria. Fukushima J. Med. Sci. 36:29–40.

Maggi, M., Vannelli, G. B., Peri, A., Brandi, M. L., Fantoni, G., Giannini, S., Torrisi, C., Guardabasso, V., Barni, T., Toscano, V. et al. (1991) Immunolocalization, binding, and biological activity of endothelin in rabbit uterus: Effect of ovarian steroids. Am. J. Physiol. 260:E292–305.

Romero, R., Avila, C., Edvin, S. S., Mitchell, M. D. (1991) Endothelin-1,2 levels are increased in the amniotic fluid of women with preterm labor and microbial invasion of the amniotic cavity. Am. J. Obstet. Gynecol. 166:95–99.

Mitchell, M. D., Lundin-Schiller, S., Edwin, S. S. (1991) Endothelin production by amnion and its regulation by cytokines. Am. J. Obstet. Gynecol. 165:120–24.

Economos, K., MacDonald, P. C., Casey, M. L. (1992) Endothelin-1 gene expression and protein biosynthesis in human endometrium: potential modulator of endometrial blood flow. J. Clin. Endocrinol. Metab. 74(1):14–9.

Ohbuchi, H., Nagai, K., Yamaguchi, M., Kitamura, K., Araki, N., Toshimori, K., lkenoue, T., Mori, N. (1992) Endothelin-1 in human uterine tissue during the menstrual cycle. Soc. Gynecol. Invest., Scientific Program and Abstracts, 39th Annual Meeting, San Antonio, Tex., March 18–21, 1992, Abstract 602.

Davenport, A. P., Cameron, I. T., Smith, S. K., Brown, M. J. (1991) Binding sites for iodinated endothelin-1, endothelin-2, and endothelin-3 demonstrated on human uterine glandular epithelial cells by quantitative high resolution autoradiography. J. Endocrinol. 129:149–154.

MacDonald, P. C., Dombroski, R. A., Casey, L. (1991) Recurrent secretion of progesterone in large amounts: An endocrine/metabolic disorder unique to young women? Endocr. Rev. 12(4):372–401.

Casey, M. L., Hemsell, D. L., MacDonald, P. C., Johnston, J. M. (1989) NAD+-dependent 15-hydroxy prostaglandin dehydrogenase activity in human endometrium. Prostaglandins 19:115–22.

Casey, M. L., Smith, J. W., Nagai, K., Hersh, L. B., MacDonald, P. C. (1991) Progesterone-regulated cyclic modulation of membrane metalloendopeptidase (enkephalinase) in human endometrium. J. Biol. Chem. 266(34):23041–23047.

Casey, M. L., Nagai, K., MacDonald, P. C. (1992) The endothelin/enkephalinase system of human endometrium: Transforming growth factor-β(TGFβ)-mediated suppression of enkephalinase expression in endometrial stromal (ES) cells. Soc. Gynecol. Invest., Scientific Program and Abstracts, 39th Annual Meeting, San Antonio, Tex., Mar. 18–21, 1992, Abst. 600.

Bukowski, R., Scholz, P., Hasan, S. H., Chwalisz, K. (1993) Induction of preterm parturition with the interleukin 1β(1L-1β), tumor necrosis factor-a (TNF-a) and with LPS in guinea pigs. Soc. Gynecol. Invest., Toronto, Ontario, Abst. S26.

Garfield, R. E., Yallampalli, C., Buhumishi, I., Chwalisz, K. (1994) Reversal of preeclampsia symptoms induced in rats by nitric oxide inhibition with Larginine, steroid hormones and an endothelin antagonist. Soc. Gynecol. Invest., Chicago, Ill., Abst. P384.

Böttcher, I., Jagher, B., Rordorf-Adam, Ch., Grüininger, M. (1987) The anti-inflammatory phaarmacologic profile of CGP 28 237 (5-methylsulfonylamino-6-phenoxy-1-indanone). Agents and Actions 21,235–237.

Wiesenberg-Böttcher, I., Schweizer, A., Green, J. R., Mueller, K., Maerki, F., Pfeilschifter, J. (1989) The pharmacological profile of CGP 28238, a novel highly potent anti-inflammatory compound. Drugs Exptl. Clin. Res. XV:501–509.

R. Romero et al., Am. J. Obstet. Gynecol. 166:95–99 (1992).

Reitz, D. B., Li, J. J., Norton, M. B., Reinhard, E. J., Collins, J. T., Anderson, G. D., Gregory, S. A., Koboldt, C. D., Perkins, W. E., Seibert, K., Isakson, P. (1994) Selective cycolooxygenase inhibitors: Novel 1,2-diarylcyclopentenes are potent and orally active COX-2 inhibitors. J. Med. Chem. 37:3878–3881.

Zimmerli, W., Sansano, S., Wiesenberg-Böttcher, I. (1991) Influence of the anti-inflammatory compound Flosulide on granulocyte function. Biochem. Pharmacol. 42:1913–1919.

Mitchell, J. A., Akarasereenont, P., Thiemermann, C., Flower, R. J., Vane, J. R. (1993) Selectivity of nonsteroid anti-inflammatory drugs as inhibitors of constitutive and inducible cyclooxygenase. Proc. Natl. Acad. Sci. U.S.A. 90:11693–11697.

"Nitrates and other Anti-angina Agents" in Martindale: The Extra Pharmacopoeia, 13$_{th}$ Edition, J. E. F. Reynolds, ed., The Pharmaceutical Press, London (1993).

S. A. Douglas et al., TiPS 15(9):313–316 (1994).

Warner et al., "Selective Endothelin Receptor Agonists and Antagonists Suggest 3 Endothelial Receptors," Third International Conference on Endothelin, Houston, Tex., Feb. 15–17, 1993, Abstract Book.

Clozel et al., "Pathophysiological Role of Endothelin Revealed by the First Orally Active Endothelin Receptor Antagonist," Nature, 365:759–761 (1993).

Haynes and Webb, (1993) "The Endothelin Family of Peptides: Local Hormones with Diverse Roles in Health and Disease," Clinical Science, 84:485–500

R. A. Atkinson and J. P. Pelton, (1992) FEBS 296:1–6.

K. Nakamichi et al., (1992) Biochem. Biophys. Res. Commun. 182:144–150.

What is claimed is:

1. A pharmaceutical composition comprising synergistically effective amounts of
    (a) an endothelin antagonist, an endothelin synthase inhibitor, or both, in combination with
    (b) at least one of a progestin, an estrogen, a combination of a progestin and an estrogen, a cyclooxygenase inhibitor, or a nitric oxide (NO) donor, an NO substrate, or both,
together with a pharmaceutically acceptable excipient.

2. A method of treating a menstrual disorder in a non-pregnant female mammal, comprising administering to the female in need of such treatment an effective amount of a composition of claim 1.

3. A method of claim 2, wherein the female is a human suffering from dysmenorrhea.

4. A method of claim 2, wherein the female mammal is a human and (a) is an endothelin antagonist.

5. A method of claim 4, wherein the endothelin antagonist is BQ-123.

6. A method of claim 2, wherein the female mammal is a human and (a) is an endothelin synthase inhibitor.

7. A method of claim 6, wherein the endothelin synthase inhibitor is SQ 28 608.

8. A method of claim 2, wherein the female mammal is a human and (b) is a progestin.

9. A method of claim 8, wherein the progestin is progesterone.

10. A method of claim 2, wherein the female mammal is a human and (b) is an NO donor or NO substrate.

11. A method of claim 10, wherein the NO substrate is L-arginine.

12. A method of claim 2, wherein the endothelin antagonist is administered orally.

13. A method of claim 2, wherein the endothelin synthase inhibitor is administered orally.

14. A method of treating preterm labor, preeclampsia or fetal growth retardation in a pregnant female mammal, comprising administering to the female in need of such treatment an effective amount of a composition of claim 1.

15. A method of claim 14, wherein the female mammal is a human suffering from preterm labor.

16. A method of claim 14, wherein the female mammal is a human female suffering from preeclampsia or fetal growth retardation.

17. A method of claim 14, wherein the female mammal is a human and (a) is an endothelin antagonist.

18. A method of claim 11, wherein the endothelin antagonist is BQ-123.

19. A method of claim 14, wherein the female mammal is a human and (a) is an endothelin synthase inhibitor.

20. A method of claim 19, wherein the endothelin synthase inhibitor is SQ 28 608.

21. A method of claim 14, wherein the female mammal is a human and (b) is a progestin.

22. A method of claim 14, wherein the progestin is progesterone.

23. A method of claim 14, wherein the female mammal is a human and (b) is an NO donor or NO substrate.

24. A method of claim 23, wherein the NO substrate is L-arginine.

25. A method of claim 14, wherein the endothelin antagonist is administered orally.

26. A method of claim 14, wherein the endothelin synthase inhibitor is administered orally.

27. A composition of claim 1, wherein (a) is an endothelin antagonist.

28. A composition of claim 27, wherein the endothelin antagonist is BQ-123.

29. A composition of claim 1, wherein (a) is an endothelin synthase inhibitor.

30. A composition of claim 29, wherein the endothelin synthase inhibitor is SQ 28 608.

31. A composition of claim 1, wherein the progestin is progesterone.

32. A composition of claim 31, wherein the cyclooxygenase inhibitor is aspirin.

33. A pharmaceutical composition of claim 1, comprising
    (a) an endothelin antagonist, an endothelin synthase inhibitor, or both, and
    (b) a progestin, an estrogen, or a combination of an estrogen and a progestin, or
    (c) a nitric oxide donor, a nitric oxide substrate, or both, or both (b) and (c),
and, optionally, a cyclooxygenase inhibitor, together with a pharmaceutically acceptable excipient.

34. A method of treating atherosclerotic vascular disease or hypertension in a male or female mammal, comprising administering to the mammal in need of such treatment an effective amount of a composition of claim 33, wherein, when the mammal is male, component (b) does not include an estrogen.

35. A method of claim 34, wherein the mammal is a human female suffering from hypertension, and (b) is an estrogen or a combination of an estrogen and a progestin.

36. A method of claim 34, wherein the mammal is a human male suffering from hypertension, and (b) is a progestin.

37. A method of claim 34, wherein the mammal is a human and (a) is an endothelin antagonist.

38. A method of claim 37, wherein the endothelin antagonist is BQ-123.

39. A method of claim 34, wherein the mammal is a human and (a) is an endothelin synthase inhibitor.

40. A method of claim 39, wherein the endothelin synthase inhibitor is SQ 28 608.

41. A method of claim 34, wherein the mammal is a human female suffering from atherosclerotic vascular disease and (b) is an estrogen or a combination of an estrogen and a progestin.

42. A method of claim 34, wherein the mammal is a human male suffering from atherosclerotic vascular disease and (b) is a progestin.

43. A method of claim 34, wherein the mammal is a human and the composition includes a nitric oxide donor and/or nitric oxide substrate.

44. A method of claim 34, wherein the progestin is progesterone.

45. A method of claim 34, wherein the nitric oxide donor and/or nitric oxide substrate are nitroglycerin and L-arginine, respectively.

46. A method of claim 34, wherein the endothelin antagonist is administered orally.

47. A method of claim 34, wherein the endothelin synthase inhibitor is administered orally.

48. A method of providing hormone replacement therapy in a female mammal, comprising administering to the female in need of such treatment an effective amount of a composition of claim 33.

49. A method of claim 48, wherein the female mammal is a human female, and (b) is a progestin or a combination of an estrogen and a progestin.

50. A method of claim 48, wherein the female mammal is a human and (a) is an endothelin antagonist.

51. A method of claim 39, wherein the endothelin antagonist is BQ-123.

52. A method of claim 48, wherein the female mammal is a human and (a) is an endothelin synthase inhibitor.

53. A method of claim 52, wherein the endothelin synthase inhibitor is SQ 28 608.

54. A method of claim 48, wherein the female mammal is a human and the composition includes a nitric oxide donor and/or nitric oxide substrate.

55. A method of claim 48, wherein the progestin is progesterone.

56. A method of claim 48, wherein the nitric oxide donor and/or nitric oxide substrate are nitroglycerin and L-arginine, respectively.

57. A method of claim 48, wherein the endothelin antagonist is administered orally.

58. A method of claim 48, wherein the endothelin synthase inhibitor is administered orally.

59. A composition of claim 53, wherein (a) is an endothelin antagonist.

60. A composition of claim 59, wherein the endothelin antagonist is BQ-123.

61. A composition of claim 59, wherein (a) is an endothelin synthase inhibitor.

62. A composition of claim 61, wherein the endothelin synthase inhibitor is SQ 28 608.

63. A composition of claim 33, wherein the progestin is progesterone.

64. A composition of claim 33, wherein the nitric oxide donor and/or nitric oxide substrate are nitroglycerin and L-arginine, respectively.

* * * * *